United States Patent
Woehr

(10) Patent No.: US 10,463,839 B2
(45) Date of Patent: *Nov. 5, 2019

(54) CATHETER DEVICE WITH NEEDLE GUARD

(71) Applicant: B. Braun Melsungen AG, Melsungen (DE)

(72) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/836,615

(22) Filed: Dec. 8, 2017

(65) Prior Publication Data

US 2018/0099123 A1    Apr. 12, 2018

Related U.S. Application Data

(63) Continuation of application No. 14/986,966, filed on Jan. 4, 2016, now Pat. No. 9,962,525, which is a
(Continued)

(30) Foreign Application Priority Data

Jul. 15, 2009 (DE) .................... 20 2009 009 602 U

(51) Int. Cl.
*A61M 5/32*    (2006.01)
*A61M 5/00*    (2006.01)
(Continued)

(52) U.S. Cl.
CPC .... *A61M 25/0606* (2013.01); *A61M 25/0075* (2013.01); *A61M 25/0084* (2013.01);
(Continued)

(58) Field of Classification Search
CPC ...... A61M 25/0084; A61M 2025/0089; A61M 25/0075; A61M 25/0097; A61M 25/0631; A61M 39/1011; A61M 5/3232
See application file for complete search history.

(56) References Cited

U.S. PATENT DOCUMENTS 5,702,367 A    12/1997    Cover et al.
5,755,709 A    5/1998    Cuppy
(Continued)

FOREIGN PATENT DOCUMENTS

DE    69824968    8/2005
EP    0922466    6/1999
(Continued)

OTHER PUBLICATIONS

International Search Report completed Nov. 1, 2010 and dated Nov. 8, 2010 from related International Application No. PCT/EP2010/004298 filed Jul. 14, 2010 (7 pages).
(Continued)

*Primary Examiner* — Rebecca E Eisenberg
(74) *Attorney, Agent, or Firm* — Klein, O'Neill & Singh, LLP

(57) ABSTRACT

The present disclosure relates to a catheter device comprising a catheter hub in which a valve member is disposed, a needle fixed in a needle hub, the needle extending through the valve member in the catheter hub in a ready position, and a tubular receptacle in which the needle hub is displaceably guided and biased by a spring in a proximal direction relative to the receptacle, wherein the needle hub is releasably held in the ready position in the receptacle against the force of the spring by frictional force between needle circumference and catheter or catheter hub, which frictional force is reduced on retraction of the needle through the catheter hub such that the force of the spring prevails.

32 Claims, 3 Drawing Sheets

Related U.S. Application Data continuation of application No. 14/193,218, filed on Feb. 28, 2014, now Pat. No. 9,227,038, which is a continuation of application No. 13/381,842, filed as application No. PCT/EP2010/004298 on Jul. 14, 2010, now Pat. No. 8,728,030.

(51) Int. Cl.
*A61M 25/06* (2006.01)
*A61M 39/10* (2006.01)
*A61M 25/00* (2006.01)

(52) U.S. Cl.
CPC .... *A61M 25/0097* (2013.01); *A61M 25/0631* (2013.01); *A61M 39/1011* (2013.01); *A61M 5/3232* (2013.01); *A61M 2025/0089* (2013.01)

(56) References Cited

U.S. PATENT DOCUMENTS

| | | | |
|---|---|---|---|
| 6,077,244 | A | 6/2000 | Botich et al. |
| 6,921,391 | B1 | 7/2005 | Barker et al. |
| 7,354,422 | B2 | 4/2008 | Riesenberger et al. |
| 7,601,139 | B2 | 10/2009 | Woehr et al. |
| 8,100,858 | B2 | 1/2012 | Woehr et al. |
| 8,328,762 | B2 | 12/2012 | Woehr et al. |
| 8,382,721 | B2 | 2/2013 | Woehr et al. |
| 8,419,688 | B2 | 4/2013 | Woehr et al. |
| 2005/0131350 | A1 | 6/2005 | Shaw et al. |
| 2016/0008580 | A1 | 1/2016 | Woehr et al. |

FOREIGN PATENT DOCUMENTS

| | | |
|---|---|---|
| EP | 1240916 A1 | 9/2002 |
| EP | 0812602 | 9/2003 |
| EP | 1545681 | 6/2005 |
| EP | 1604700 | 9/2010 |
| JP | H 10-15075 A | 1/1998 |
| JP | H11-4894 A | 1/1999 |
| JP | 2001-522658 A | 11/2001 |
| JP | 2005/004973 | 1/2005 |
| JP | 2008-200161 | 9/2008 |
| JP | 5782437 B | 9/2015 |
| WO | WO 97/45151 | 12/1997 |

OTHER PUBLICATIONS

Written Opinion completed Nov. 1, 2010 and dated Nov. 8, 2010 from related International Application No. PCT/EP2010/004298 filed Jul. 14, 2010 (7 pages).
International Preliminary Report on Patentability on corresponding PCT application (PCT/EP2010/004298) from International Searching Authority (EPO) dated Jan. 26, 2012.
Notice of Allowance dated Feb. 19, 2014 from corresponding U.S. Appl. No. 13/381,842.
Final Office Action dated Dec. 23, 2013 from corresponding U.S. Appl. No. 13/381,842.
Office Action dated Jun. 20, 2013 from corresponding U.S. Appl. No. 13/381,842.
Non-Final Office Action on co-pending (U.S. Appl. No. 14/193,218) dated Jul. 6, 2015.
Notice of Allowance on co-pending (U.S. Appl. No. 14/193,218) dated Nov. 18, 2015.
Search Report on corresponding foreign application (DE Application No. 20 2009 009 602.5) from the German Patent Office dated Jul. 15, 2009.
Office Action dated Aug. 14, 2014 from related European Patent Application No. 10 734 919.3 (4 pages).
Examiner's Report on corresponding foreign application (EP Application No. 10 734 919.3) from the European Patent Office dated Nov. 28, 2016.
Office Action on corresponding foreign application (JP Application No. 2012-519929) from the Japanese Patent Office dated May 7, 2014.
Examiner's Report on corresponding foreign application (JP Application No. 2012-519929) from the Japanese Patent Office dated Jan. 6, 2015.
Decision to Grant on corresponding foreign application (JP Application No. 2012-519929) from the Japanese Patent Office dated Jul. 14, 2015.
Examiner's Report on corresponding foreign application (JP Application No. 2015-095142) from the Japanese Patent Office dated Apr. 19, 2016.

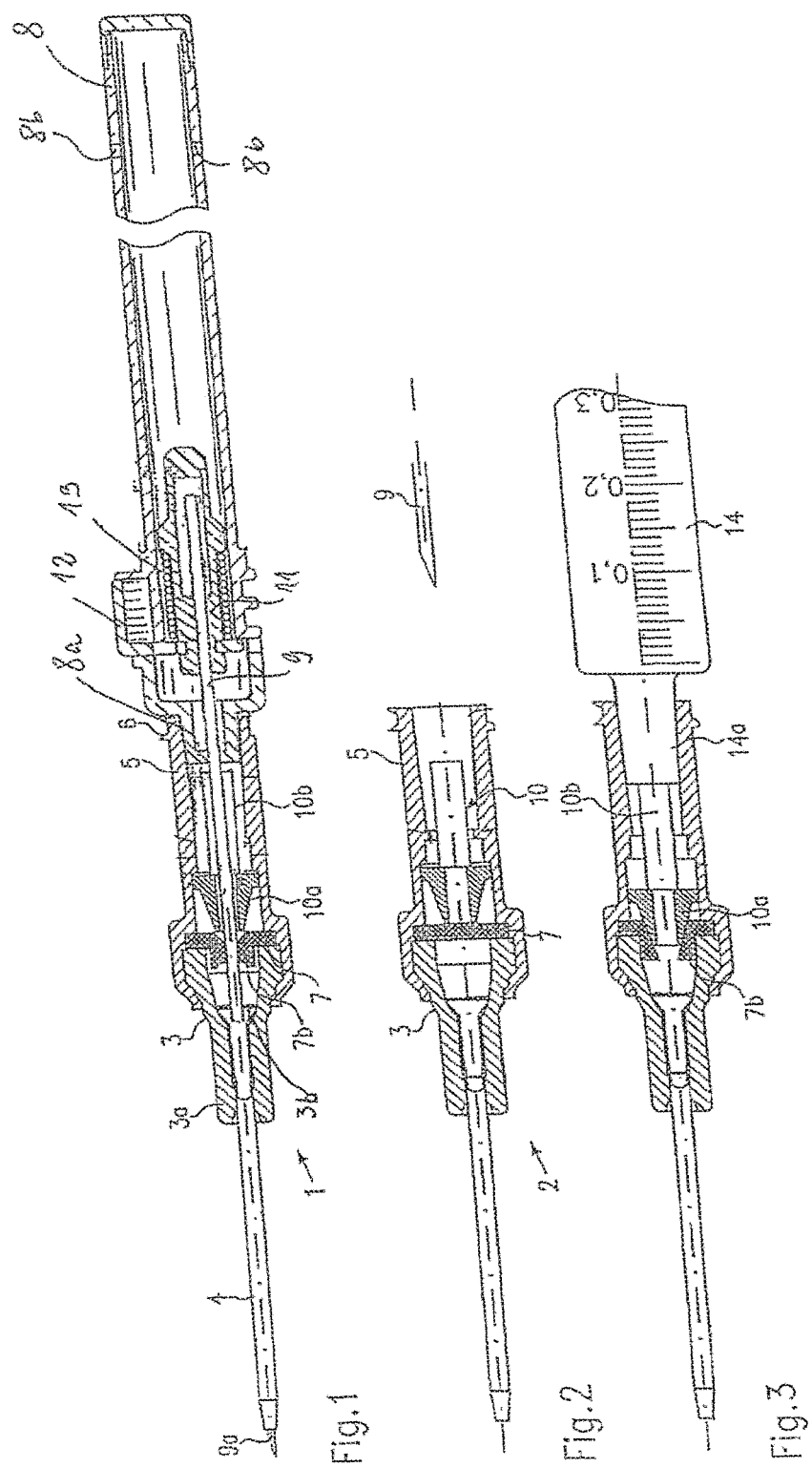

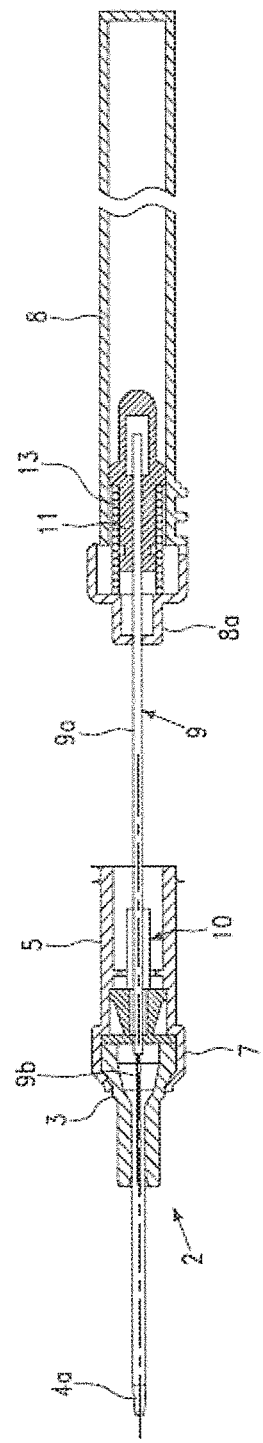
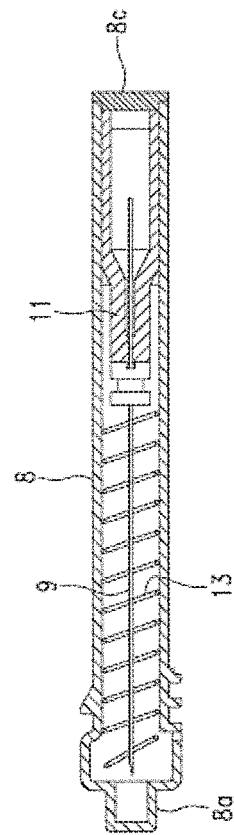

CATHETER DEVICE WITH NEEDLE GUARD

CROSS-REFERENCE TO RELATED APPLICATIONS

This is a continuation application of Ser. No. 14/986,966, filed Jan. 4, 2016, which is a continuation of application Ser. No. 14/193,218, filed Feb. 28, 2014, which is a continuation application of Ser. No. 13/381,842, filed Feb. 6, 2012, which is a national phase application under 35 U.S.C. § 371 of PCT Application No. PCT/EP2010/004298, filed Jul. 14, 2010, which claims the benefit of German application No. 20 2009 009 602.5 filed Jul. 15, 2009, the contents of each of which are expressly incorporated herein by reference.

FIELD OF ART

The present disclosure relates to a catheter device in which the needle retracted from the catheter is brought into a protective position inside a tubular receptacle.

BACKGROUND

EP 922 466 describes a catheter device of this kind wherein, in the ready position, the tubular receptacle for the needle engages a catheter hub via a projection at the distal end. A needle hub is displaceable inside the receptacle, and in the ready position this needle hub is impinged on by a spring and held in a distal position in the receptacle by a locking member. After the catheter has been inserted in a patient, the receptacle with the needle is withdrawn from the catheter hub, wherein the lock on the needle hub is released by the manually operated locking member, so that the needle hub is moved into a proximal position in the receptacle by the spring, in which position the needle tip is located in the protective position inside the receptacle, which at the distal side is provided with only a through hole for the passage of the needle.

From EP 1 240 916 it is known to provide in a catheter hub a valve member through which the needle extends in the ready position, and which automatically closes the catheter hub after retraction of the needle from the catheter hub such that no blood can emerge from the catheter hub. By means of a valve actuation member mounted displaceably in the catheter hub, the valve member can be re-opened when a syringe or an intravenous line is inserted in the catheter hub thereby displacing the valve actuating member into the open position.

SUMMARY

According to the present method, system and device, a needle which can be retracted into a receptacle is provided with a catheter device in whose catheter hub a valve member is disposed, which closes the catheter hub after removal of the needle and which can be brought into the open position when a syringe or intravenous line is inserted.

Further aims, advantages, features and possible applications of the present method, system and device become apparent from the following description of the embodiments with reference to the drawings.

Hereby, all the features described and/or shown diagrammatically form the subject matter of the present method, system and device, whether in themselves or in any meaningful combination, and independently of their summary in the claims and of the back-referencing of the claims.

BRIEF DESCRIPTION OF THE FIGURES

An exemplary embodiment of the present method, system and device is explained in more detail below with reference to the drawings, in which:

FIG. 1 shows a longitudinal section through a catheter device having a needle inserted therein in the ready position, FIG. 2 shows a view of the catheter device with the needle retracted and removed therefrom, FIG. 3 shows a syringe inserted in the catheter hub, FIG. 5 shows the embodiment of FIG. 4 during the retraction of the needle, and FIG. 6 shows the needle in the protective position.

DETAILED DESCRIPTION

Figure 4:
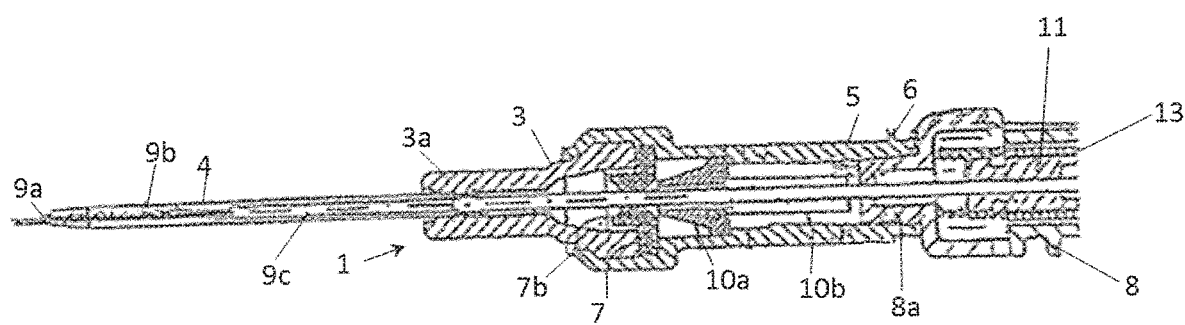
FIG. 4 shows an embodiment with a needle portion which supports sliding properties, in the ready position.

FIG. 1 shows a catheter insertion device 1 having a catheter hub 2, which is configured in two parts in the embodiment shown. A distal hub member 3 of the catheter hub has a holding portion 3a in which a catheter 4 is press-fitted by means of a funnel-shaped sleeve 3b. The proximal end of the hub member 3 has an enlarged diameter in relation to the distal end and forms a joining portion to a hub member 5, whose distal end engages the proximal end of the hub member 3 and which is provided at its proximal end with a Luer thread 6. Between the two hub members 3 and 5, a non-return valve is inserted in the form of a valve disc 7 which is fixed in its position by the two hub members 3 and 5. The catheter hub 2 can also be configured as one piece, wherein the valve disc 7 can be press-fitted therein.

In the ready position according to FIG. 1, there is inserted in the catheter hub 2 a receptacle 8 having a nose-shaped axially projecting boss 8a in which a hollow needle 9 is fixed in a needle hub 11. In the embodiment shown, the boss 8a is a separate piece, by means of which assembly is facilitated. It is also possible to mould the boss 8a on the receptacle 8 and to configure the proximal wall 8c as a cap or separate piece, by means of which assembly is facilitated. The needle 9 extends through the valve disc 7 and the catheter 4 so that the needle tip 9a is exposed. Between boss 8a and valve disc 7, a valve actuation member 10 is displaceably disposed in the proximal hub member 5 and has a truncated cone-shaped abutting portion 10a which serves to open the valve disc 7. On the proximal side, a push portion 10b is attached to the abutting portion 10a.

When the hollow needle 9 is retracted from the catheter hub 2, the valve disc 7, due to its resilience, closes the through hole for the hollow needle 9, as the separated position represented in FIG. 2 shows, so that no blood can emerge from the catheter 4. The silicon valve disc is provided, for example, with three slits starting from the middle and extending radially over a short portion to form resilient lugs 7b therebetween which can be widened by the hollow needle. Other embodiments of a valve are also possible, wherein a different number of slits can also be provided.

FIG. 3 shows a syringe 14 inserted in the catheter hub 2 and having a distally protruding luer taper 14a which is configured longer than the boss 8a at the receptacle 8, so that the valve actuating member 10 is displaced into the open position in FIG. 3.

The needle hub 11 is displaceably guided in the tubular receptacle 8 and held in the ready position in FIG. 1 by a locking member 12 against the force of a spring 13 which biases the needle hub 11 in the proximal direction. After the locking member 12 is released by pressure transverse to the receptacle 8, the needle hub 11 is displaced in the receptacle in a proximal direction by the spring 13.

FIGS. 4 and 5 show an embodiment in which a locking member 12 releasing the connection is not provided between the needle hub 11 and the receptacle 8. The spring-biased needle hub 11 is held in the ready position shown in FIG. 4 only by frictional force between the valve member 7 and the needle circumference and possibly by frictional force between the catheter tip 4a and the needle 9, wherein this frictional force is designed to be larger than the force of the spring 13. For this, the needle circumference can also be provided on the longitudinal portion 9c with a coating or surface treatment which increases the friction, to generate a correspond-ding frictional force between the valve member 7 and the needle circumference.

In addition or alternatively to this, the valve member 7 can be designed such that, for example, by means of lengthening the lugs 7b abutting at the needle circumference and corresponding surface treatment of the valve member, the frictional force between the needle circumference and the valve member 7 has the required strength, which is larger than the force of the spring 13 which impinges the needle hub 11 in the receptacle 8 in the proximal direction.

On a distal end portion 9b of the needle 9 in FIGS. 4 and 5, a coating or surface treatment is provided to reduce the friction between the needle circumference and the valve member 7 and between the catheter tip 4a and the needle 9, so that when the needle 9 is retracted from the catheter hub 5 (FIG. 5) a reduction in friction occurs between the uncoated area 9c of the needle 9 and the valve member 7 and the coated area 9b and valve member 7, by means of which the spring 13 is released. As soon as the portion 9b of the needle 9 which is provided with a sliding coating or corresponding surface treatment reaches the valve member 7, the force of the spring 13 becomes greater than the frictional force between this portion 9b of the needle circumference and the valve member 7, so that the holding effect in relation to the spring 13 is cancelled and the spring is released.

The needle can also have a uniform surface condition over its whole length, wherein the spring 13 only displaces the needle hub back into the receptacle 8 after the needle has been retracted through the narrowed tip 4a of the catheter 4 and there is no more additional frictional force between the needle 9 and the catheter tip 4a. The distal end portion 4a of a usual catheter 4 has a diameter which is slightly smaller than the outer diameter of the needle. On the remaining area, the catheter 4 is provided with an inner diameter which is larger than the outer diameter of the needle.

According to a further embodiment, a friction member (not shown) can be disposed in the catheter hub, preferably distally before the valve member 7, to exert a predetermined frictional force on the needle circumference so long as the friction member is acting on the needle circumference. When the needle 9 is retracted so far back that it is no longer impinged by the friction member, the friction force effecting the holding force for the spring 13 is reduced, so that the spring 13 moves the needle hub 11 into the proximal protective position in the receptacle 8.

Such a friction member can be provided in the catheter hub 2, either in addition to the embodiment of a low friction portion 9b or instead of the friction-reducing portion 9b of the needle.

Such a friction member can, for example, be a friction member which is impinged on by a radially acting spring and which presses onto the circumference of the needle 9 It is also possible to mount a friction member or friction members at the lugs 7b of the valve member 7, preferably on the distal side thereof, so that when the valve member 7 is opened by the valve actuating member 10, the friction members abutting at the needle circumference are moved out of the passage cross-section of the catheter hub when the syringe 14 is inserted (see FIG. 3).

An embodiment is also possible in which no valve actuating member 10 is provided in the catheter hub 2, but instead the valve member 7 is moved into the open position, for example, by positive pressure or negative pressure exerted by the syringe 14.

Furthermore, the receptacle 8 can be configured in a different way in connection with the needle hub 11 which is held only by frictional force in its ready position outside the receptacle 8. In FIG. 1, 8b designates vent openings for air to escape when the needle hub 11 is moved quickly by the spring 13 into the proximal protective position. Reference numeral 8c designates a cap. By way of example, the needle hub 11 can also be provided with a friction portion by means of which, in the ready position in FIG. 4, the holding force is maintained in connection with the frictional force in the catheter hub, whereupon on cessation of the frictional force in the catheter hub, the force of the spring 13 exceeds the frictional force of the needle hub 11 in the receptacle 8 and moves the needle hub into the protective position.

In FIG. 5, a distance between the catheter hub 2 and the receptacle 8 is represented which can only occur when the user holds the catheter hub 2 in one hand and also holds the receptacle 8 at a distance from the catheter hub 2 in the other hand. If the receptacle 8 is not held at a distance from the catheter hub 2, the spring 13 urges the receptacle 8 against the proximal end of the catheter hub. This has the advantage for the user that the needle portion 9c is covered while the needle is only partly retracted from the catheter hub 2 and, for example, the catheter hub 2 is fixed on the patient with adhesive tape. After this, the receptacle 8 can be retracted past the position represented in FIG. 5 until the spring 13 is released due to cessation of the frictional force in the catheter hub 2 and the needle is retracted in the receptacle 8.

The invention claimed is:

1. A catheter device comprising:
   a catheter hub having a body having a catheter tube attached to the body and extending in a distal direction, said body defining an interior;
   a valve member disposed in the interior of the catheter hub, said valve member having a wall with a proximally facing wall surface, a distally facing wall surface, and a plurality of slits formed through the wall and defining resilient lugs;
   a needle fixed to a needle hub, the needle having a needle tip and a needle shaft extending through the valve member and the catheter hub with the needle tip extending out a distal tip of the catheter tube in a ready position;
   a tubular receptacle having a body defining an interior in which the needle hub is disposed, said needle hub is releasably held against a spring force of a spring in the ready position and the needle hub is displaceably guided by the spring in a proximal direction when the spring is released; and
   wherein the spring is held in a compressed state by a releaseable locking member located at a distal end of the tubular receptacle when in the ready position, said releaseable locking member having a surface for pressing by a user.

2. The catheter device according to claim 1, wherein the valve member has at least three slits forming the resilient lugs.

3. The catheter device according to claim 2, wherein the valve member is held in a groove, between two shoulders.

4. The catheter device according to claim 1, wherein the releaseable locking member is released by pressure applied to the surface and the pressure is transverse to a lengthwise axis of the tubular receptacle.

5. The catheter device according to claim 1, further comprising a valve actuating element comprising a nose section and a plunger section, said nose section being sized and shaped to open the plurality of slits.

6. The catheter device according to claim 5, wherein the valve actuating element comprises a flange located distally of a shoulder inside the interior of the catheter hub to limit proximal travel of the valve actuating element.

7. The catheter device according to claim 1, wherein the catheter hub comprises a distal hub member attached to a proximal hub member.

8. The catheter device according to claim 1, wherein the valve actuating element comprises a cone-shaped abutting portion for opening the valve member.

9. The catheter device according to claim 1, further comprising an axially projecting boss projecting into the catheter hub.

10. The catheter device according to claim 9, wherein the projecting boss is a separate piece attached to the tubular receptacle.

11. The catheter device according to claim 1, wherein an axially projecting boss is integrally formed with the tubular receptacle.

12. The catheter device according to claim 1, further comprising a vale actuating element located inside the catheter hub and distal of the needle hub, said valve actuating element comprising a flange located between a distal shoulder and a proximal shoulder.

13. The catheter device according to claim 1, further comprising a valve actuating member located inside the catheter hub between the valve and an axially projecting boss extending distally of the tubular member and into the interior of the catheter hub.

14. The catheter device according to claim 1, wherein the surface of the releasable locking member projects outwardly of an exterior surface of the tubular receptacle prior to the spring displacing the needle hub into the tubular receptacle.

15. A catheter device comprising:
a catheter tube attached to a catheter hub, said catheter hub having a body defining an interior and an open proximal end;
a valve member is disposed in the interior of the catheter hub;
a needle fixed to a needle hub, said needle having a needle tip and a needle shaft, said needle shaft extending through the valve member and the needle hub with the needle tip extending distally of a distal opening of the catheter tube in a ready position;
a tubular receptacle having a body defining an interior in which the needle hub is displaceably guided and biased in a proximal direction by a spring;
wherein the needle hub is releasably held inside the tubular receptacle against a spring force and the spring is held in a compressed state by a manually operated locking member, said manually operated locking member having a surface for pressing by a user; and
wherein the valve member comprises at least three slits forming resilient lugs that are deformed by the needle shaft in the ready position.

16. The catheter device according to claim 15, wherein the locking member is releaseable by pressure applied to the surface and the pressure is transverse to a lengthwise axis of the tubular receptacle to release the spring to thereby allow the spring to expand.

17. The catheter device according to claim 16, wherein the locking member is located at a distal end of the tubular receptacle.

18. The catheter device according to claim 15, further comprising a projecting boss formed as a separate piece from the tubular receptacle and projecting into the catheter hub.

19. The catheter device according to claim 18, wherein the projecting boss is a separate piece from the locking member.

20. The catheter device according to claim 15, further comprising a valve actuating element comprising a nose section for opening the valve and a plunger section, said valve actuating element is displaceably disposed inside the catheter hub.

21. The catheter device according to claim 20, wherein the nose section is a truncated cone-shaped abutting portion for opening the valve member.

22. The catheter device according to claim 15, wherein the catheter hub comprises a distal hub member attached to a proximal hub member.

23. The catheter device of claim 15, further comprising a valve actuating element sized and shaped to be located inside the catheter hub, distal of a projecting boss projecting distally of the tubular receptacle.

24. The catheter device of claim 23, wherein the valve actuating element comprises a nose section for pushing against the valve, a plunger section, and a flange having a radially projecting surface.

25. The catheter device of claim 24, wherein the flange is located distal of a shoulder inside the interior of the catheter hub to limit proximal travel of the valve actuating element.

26. The catheter device of claim 25, wherein the plunger section comprises one or more gaps for fluid flow thereacross or therethrough.

27. The catheter device of claim 23, wherein the valve is located between two shoulders.

28. A method of assembling a catheter device comprising:
placing a releasable locking member having a surface for pushing at a distal location on a tubular receptacle to release a coil spring; said tubular receptacle having a body defining an interior and said coil spring being held in a compressed state by the releasable locking member and said coil spring expandable to move a needle hub having a needle attached thereto in a proximal direction inside the interior of the tubular receptacle when released by the releasable locking member;
placing a catheter hub having a catheter tube in mechanical communication with the needle so that the needle projects through the needle hub and through the catheter tube and a tip of the needle extends out a distal opening of the catheter tube; said catheter hub having an interior having a valve member having a plurality of slits defining a plurality of resilient lugs and a valve actuating element disposed therein; said valve actuating element comprising a nose section having a surface for pushing against the valve and a plunger section having a plunger end surface configured to be pushed so that the nose section deflects the plurality of resilient lugs; and wherein the needle is separable from the catheter hub and the catheter tube by pressing the releasable locking member; and wherein a proximal opening of the catheter hub is exposed when the needle hub and the tubular receptacle are separated from the catheter hub.

29. The method of claim 28, wherein the catheter hub comprises a distal hub member attached to a proximal hub member.

30. The method of claim 28, wherein a projecting boss extends distally of the tubular member and into the interior of the catheter hub.

31. The method of claim 28, wherein the interior of the catheter hub has a distal shoulder and a proximal shoulder and wherein a flange located on the valve actuating element is located between the proximal and distal shoulders.

32. The method of claim 31, wherein the flange is movable between the proximal and distal shoulders.

\* \* \* \* \*